(12) United States Patent
Bohnen et al.

(10) Patent No.: US 6,685,896 B2
(45) Date of Patent: Feb. 3, 2004

(54) METHOD FOR RECOVERING RHODIUM FROM REACTION PRODUCTS OF OXOSYNTHESIS

(75) Inventors: Hans-Willi Bohnen, Moers (DE); Richard Fischer, Louisville, KY (US); Mark Hewlett, Bay City, TX (US); Wolfgang Zgorzelski, Oberhausen (DE); Norbert Schopper, Duisburg (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/181,393

(22) PCT Filed: Jan. 24, 2001

(86) PCT No.: PCT/EP01/00759

§ 371 (c)(1), (2), (4) Date: Sep. 5, 2002

(87) PCT Pub. No.: WO01/56932

PCT Pub. Date: Aug. 9, 2001

(65) Prior Publication Data

US 2003/0119923 A1 Jun. 26, 2003

(30) Foreign Application Priority Data

Feb. 4, 2000 (DE) .................................... 100 05 084

(51) Int. Cl.$^7$ .................... C22B 11/00; C07F 15/00; B01J 20/34

(52) U.S. Cl. ................... 423/22; 502/22; 502/29; 502/30; 502/31; 502/34; 556/24; 556/136

(58) Field of Search ............... 423/22; 502/22, 502/29, 30, 31, 34; 556/24, 136

(56) References Cited

U.S. PATENT DOCUMENTS

| | | | | |
|---|---|---|---|---|
| 5,206,000 A | * | 4/1993 | Diekhaus et al. | 423/22 |
| 5,264,600 A | * | 11/1993 | Lappe et al. | 556/20 |
| 5,294,415 A | | 3/1994 | Lappe et al. | 423/22 |
| 5,364,445 A | * | 11/1994 | Sakamoto et al. | 75/426 |

FOREIGN PATENT DOCUMENTS

| | | |
|---|---|---|
| DE | 1592502 | 5/1972 |
| EP | 0007768 | 2/1980 |
| EP | 0538732 | 4/1993 |
| FR | 1590393 | 4/1970 |

* cited by examiner

*Primary Examiner*—Porfirio Nazario-Gonzalez
(74) *Attorney, Agent, or Firm*—Muserlian, Lucas and Mercanti

(57) ABSTRACT

The invention relates to a method for separating and recovering rhodium from reaction products of oxosynthesis, especially reaction products containing cobalt. The invention also relates to the reuse of rhodium as a catalyst for hydroformulation and to a catalyst for hydroformulation itself. The inventive method is characterized by the following: extraction of the organic solution with an aqueous phosphate solution or a phosphate solution, water washing, oxidative treatment of the organic phase, and extraction of the organic phase with an aqueous water-soluble arylphosphine solution.

13 Claims, No Drawings

METHOD FOR RECOVERING RHODIUM FROM REACTION PRODUCTS OF OXOSYNTHESIS

This application is a 371 of PCT/EP01/00759 filed Jan. 24, 2001.

The present invention relates to an improved process for removing and recovering rhodium from oxo process reaction products.

The preparation of aldehydes and alcohols by addition of carbon monoxide and hydrogen to olefinic double bonds (hydroformylation) is well known. The reaction is catalyzed by metals or compounds thereof of the $8^{th}$ transition group of the Periodic Table which form carbonyl or hydridocarbonyls under the reaction conditions. While cobalt and cobalt compounds used to be used as catalysts, rhodium catalysts are today finding use to an increasing extent, even though rhodium is several times more expensive than cobalt. Rhodium is used alone or in combination with complexing agents, for example organic phosphines. While the oxo process requires reaction pressures of from 25 to 30 MPa using rhodium as catalyst, pressures of from 1 to 5 MPa suffice when rhodium complexes are used.

In many cases, rhodium catalysts have distinct advantages. They have higher activity and selectivity and additionally facilitate uncomplicated operation of the production plants, in particular relating to conduct of the synthesis and the excavation of the products from the reactor. Finally, the classic oxo process based on cobalt catalysts may be converted in many cases to rhodium catalysts using the available apparatus parts with only minimal capital expenditure.

Despite the advantages mentioned of the rhodium-catalyzed oxo process, the classic cobalt process continues to be operated in existing old plants, in particular when conversion of the process to the rhodium method under the given economic conditions does not appear necessary.

Particular significance attaches to the recovery of rhodium which, after the reaction has ended, is present as the carbonyl compound dissolved in the hydroformylation product. The work up comprises depressurizing the crude oxo product in more than one stage by reducing the synthesis gas pressure from about 25 to 30 MPa initially to from 1.5 to 2.5 MPa. This releases synthesis gas dissolved in the crude product. The mixture can then be depressurized to atmospheric pressure. Before purification or further processing of the reaction product, by distillation, the dissolved rhodium compounds have to be removed. It has to be taken into account here that only a few ppm of the noble metal are present homogeneously dissolved in the crude product. Also, in the course of the depressurization procedure, rhodium can be converted to a metallic form or form multinuclear carbonyl compounds which separate from the liquid organic phase as solids.

In the process known from EP-A-147824, rhodium is removed and recovered by extracting it from the crude oxo product by means of complexing reagents.

The crude oxo product is the oxo process reaction mixture obtained after depressurizing and possible cooling.

In the known process, the complexing agents used are sulfonated or carboxylated organic phosphines, preferably sulfonated arylphosphines. The sulfonated or carboxylated organic phosphines form water-soluble complexes with rhodium. Accordingly, the rhodium may be extracted from the crude organic product using an aqueous solution of the substituted phosphine.

This transfers the rhodium to the aqueous phase which can be removed by simple decanting from the organic product mixture. Circulation of the complexing agent solution provides high rhodium concentrations in the aqueous phase.

According to EP-A-156253, the process disclosed by EP-A-0147824 is improved by adding a solubilizer to the aqueous solution of the complexing agent. Its effect is in particular to alter the physical properties of the surface area between the two liquid phases and thereby to accelerate the transfer of the aqueous extractants into the product phase and that of the rhodium from the product phase into the aqueous phase. However, the effectiveness of the process described depends on the quantity of solubilizer added. Its quantity cannot be increased without limitation because the materials added unnecessarily burden the aqueous solution of the extractant and compromise its stability.

In the process disclosed by EP-B1-0 183 200, the depressurized crude oxo product is likewise extracted using an aqueous solution of a complexing agent. However, this process does not operate with the addition of a solubilizer, but instead employs sulfonated arylphosphines having quaternary ammonium counter ions, for example the benzyltrimethylammonium cation, as water-soluble complexing agents.

The prior art processes employ a catalyst solution which results from hydroformylation reactions with rhodium catalysis.

However, problems occur where a hydroformylation plant initially operated under cobalt catalysis is to be converted to rhodium catalysis.

For instance, EP-B1-0 111 257 concerns a hydroformylation process which comprises reacting the off gas from a first hydroformylation step (which reacts olefin with carbon monoxide and hydrogen in the presence of a catalyst solution comprising an aqueous rhodium complex at low pressure) in a second step by the classical oxo process at high pressure and in the presence of cobalt catalysts.

The conversion of this process to the complete rhodium method, i.e. also carrying out the/second step under rhodium catalysis, is the subject matter of EP-A1-0 805 138.

The organic phase resulting from conversion to the rhodium method accordingly comprises both rhodium and cobalt as catalytically active metal.

Since rhodium is a precious metal, there is accordingly great interest in its removal, recovery and reuse as active catalyst metal from the cobalt-containing catalyst solution for economic reasons. It is of decisive importance that the rhodium occurs virtually completely in a form which allows reuse as a catalyst component. In order to obtain highly optimal activity and selectivity for the recovered catalyst, virtually complete removal of the cobalt from the rhodium is sought. It should likewise be possible to recover rhodium virtually completely while at the same time retaining the activity and selectivity of the catalyst solution after complete removal of the cobalt from the hydroformylation process or from the oxo process reaction products which were hitherto obtained by exclusive rhodium catalysis.

It is accordingly an object of the present invention to provide a process by which rhodium may be virtually completely recovered from an organic catalyst solution in a simple manner. The catalyst solution may additionally comprise cobalt-containing compounds as impurities. At the same time, it shall be ensured that rhodium is obtained in a form suitable for reuse as catalyst. The rhodium compounds obtained shall be suitable for reuse both in a homogeneous hydroformylation process carried out in the organic phase and also in the biphasic hydroformylation process in the presence of water disclosed by DE-C-26 27 354.

This object is achieved by a process for recovering rhodium from organic solutions comprising rhodium complexes with or without cobalt complexes and with or without complexing ligands, which comprises extracting the organic phase with an aqueous solution of a phosphate of the formula $(O)P(OR^1)(OR^2)(OR^3)$, where $R^1$, $R^2$ and $R^3$ are identical or different and are hydrogen, a straight-chain or branched alkyl radical having 1–10 carbon atoms or a substituted or unsubstituted aryl radical having 6–10 carbon atoms, and the aryl radical is substituted by straight-chain or branched alkyl radicals having 1–4 carbon atoms, or with a phosphonate of the formula $R^4P(O)(OR^5)(OR^6)$, where $R^4$, $R^5$ and $R^6$ are identical or different and are hydrogen, a straight-chain or branched alkyl radical having 1–10 carbon atoms or a substituted or unsubstituted aryl radical having 6–10 carbon atoms, and the aryl radical is substituted by straight-chain or branched alkyl radicals having 1–4 carbon atoms;

washing the organic phase with water at a pH of from 0 to 8;

treating the organic phase after phase separation with an oxidizing agent at a temperature of from 0 to 100° C.;

treating the organic phase with an aqueous solution of a water-soluble arylphosphine at elevated temperature and elevated pressure;

and removing the rhodium-containing aqueous solution from the organic phase by phase separation.

The procedure according to the invention is generally suited to recovering rhodium from an organic phase. An example of such an organic phase is the crude oxo product which is the reaction mixture resulting from the hydroformylation reaction after depressurization and optional cooling, or the distillation residue of the crude oxo product after removing the aldehyde. Additionally, the organic phase may possibly also comprise cobalt compounds and/or complexing ligands, which is the case when a hydroformylation process hitherto carried out under cobalt catalysis has been converted to the rhodium method. However, the process according to the invention may also be applied to rhodium recovery when the cobalt quantity originally present has been discharged in the meantime or the hydroformylation process has always been operated under rhodium catalysis.

The organic phase introduced into the recovery process comprises, in addition to the desired aldehydes, condensation products thereof and also alcohols. Complex ligands may also possibly be present, depending on whether the old cobalt process was carried out in the presence of a complexing ligand and whether the rhodium process is carried out using complexing ligands. However, it is also possible to add complexing ligands to the organic phase resulting from the hydroformylation reaction before further work up to stabilize rhodium complexes. The complex ligands present are customary ligands in hydroformylation processes such as alkyl phosphines, alkylarylphosphines or arylphosphines, for example triphenylphosphine. Further components present may include oxides derived from the complexing ligands, for example triphenylphosphine oxide, which are dissolved in the organic phase.

The operation explained in the following describe the work up of a rhodium-containing catalyst solution which additionally comprises cobalt compounds as impurities. It will be appreciated that the procedure according to the invention can also be applied to those catalyst solutions comprising organic rhodium from which the cobalt has already been completely removed or which come from a hydroformylation process carried out in the organic phase under rhodium catalysis.

As well as cobalt, rhodium is present at a concentration of from 10 to 10 000 ppm, in particular from 100 to 5 000, preferably from 200 to 1 000 ppm by weight, based on the total mass of the solution. The cobalt content is generally from 10 to 5 000 ppm by weight, based on the total mass of the solution. In the further course of the hydroformylation process carried out under rhodium catalysis, the cobalt content falls owing to the continuous discharge from the hydroformylation process. The organic phase comprises from 1 to 20, in particular from 1 to 10, preferably from 2 to 6% by weight of complexing ligands, based on the total mass of the organic phase. In addition, there are also oxidation products of the complexing ligands, such as phosphine oxides. The concentration is generally from 1 to 10% by weight, based on the total mass of the organic phase. The organic components present include aldehydes, alcohols, aldols, condensation products and possibly olefin, if an olefin having at least 4 carbon atoms had been used for the hydroformylation reaction. Their relative quantity ratios depend on whether the crude oxo product or the distillation residue obtained therefrom is selected for the work up process according to the invention.

With the aid of the process according to the invention, it is possible to remove rhodium which is generally present in low concentration with surprisingly high selectivity and yield from the cobalt present in excess.

In the process according to the invention, cobalt is first removed from the organic phase present.

To this end, the organic phase is extracted with an aqueous solution of a phosphate of the formula $(O)P(OR^1)(OR^2)(OR^3)$. $R^1$, $R^2$ and $R^3$ are identical or different and are hydrogen, a straight-chain or branched alkyl radical having 1–10 carbon atoms, preferably 1–5 carbon atoms, or a substituted or unsubstituted aryl radical having 6–10 carbon atoms. The aryl radical may be substituted by straight-chain or branched alkyl radicals having 1–4 carbon atoms. Preference is given to using an aqueous phosphoric acid solution or an aqueous solution of trimethyl phosphate for extraction.

Aqueous phosphonate solutions can also be used in the extract step. Useful phosphonic acids include compounds of the formula $R^4P(O)(OR^5)(OR^6)$. $R^4$, $R^5$ and $R^6$ are identical or different and are hydrogen, a straight-chain or branched alkyl radical having 1–10 carbon atoms, preferably 1–5 carbon atoms, or a substituted or unsubstituted aryl radical having 6–10 carbon atoms. If the aryl radical is substituted, it carries straight-chain or branched alkyl radicals having 1–4 carbon atoms. Preference is given to using an aqueous phosphonic acid solution where $R^4$ is methyl, ethyl, propyl or butyl or an aqueous solution of methyl dimethylphosphonate for extraction.

The concentration of the extractant in the aqueous solution is variable over a wide range. In general, aqueous solutions are used where the concentration of the phosporos-containing extractants is from 1 to 95, preferably from 30 to 60% by weight, based on the aqueous extraction solution.

When the extraction of cobalt is carried out at atmospheric pressure, operation is effected at a temperature of from 0 to 100° C., preferably 20 to 40° C. However, it is also possible to treat the organic phase with aqueous extractants under pressure at temperatures of from 100 to 200° C., preferably from 120 to 140° C. When operation is effected at temperatures above 100° C., the pressure is generally from 0.5 to 20 MPa.

In order to achieve sufficient phase separation, the volume ratio of organic phase to aqueous extraction phase ranges from 20:80 to 80:20, preferably from 40:60 to 60:40. The extraction is generally carried out over a duration of from 0.5 to 5 hours, preferably from 1 to 3 hours.

The extraction step is generally repeated more than once, and the organic phase is generally extracted from 2 to 4 times in succession.

To remove remaining quantities of extractant, the treated organic phase is admixed with water at a temperature of from 0 to 100° C., preferably from 20 to 40° C. The water quantity is generally from about 25 to 50% of the volume of the organic phase present. Water washing is carried out at a pH in the range from 0–8, preferably 4–8. To adjust the washing water to the desired pH, an aqueous solution of an alkaline substance having a concentration of from 3 to 20% by weight is generally added to the washing water. Preference is given to using aqueous solutions of alkali metal hydroxides, alkaline earth metal hydroxides, alkali metal carbonates, alkaline earth metal carbonates, alkali metal hydrogen carbonates or alkaline earth metal hydrogen carbonates, in particular sodium hydroxide or potassium hydroxide.

To achieve complete phase separation, it is frequently advisable to add an organic solvent. Useful solvents include aliphatic hydrocarbons having from 6 to 12 carbon atoms, aromatic hydrocarbons having from 6 to 12 carbon atoms, aldehydes or condensation products thereof. It is particularly advisable to add exactly the aldehyde which was the target product of the oxo process. The quantity of the organic solvent added corresponds to the quantity of the organic phase treated.

The extraction to be carried out according to the inventive process with subsequent water washing and pH adjustment leads to a reduction of the cobalt content in the organic phase treated of more than 90%, based on the cobalt quantity originally present.

The organic phase present after extraction and water washing is then subjected to an oxidative treatment. The oxidation of the organic phase is carried out at temperatures of from 0 to 100° C., in particular from 30 to 60° C. and preferably from 50 to 60° C. Since the organic phase comprises aldehydes which either stem from the oxo process or have been added to support phase/separation during water washing, carboxylic acids are formed during the oxidation. The formation of the carboxylic acids and further oxidation products from the organic components is exothermic. In order to avoid an uncontrolled oxidation reaction, countercurrent cooling of the oxidation reactor may be required. In the course of the oxidation, not only the complexing ligand present in excess, but also the rhodium complex itself will be attacked, which converts the ligand to a form which is no longer suitable for complexation. The phosphine oxides arise from the phosphines generally used as complexing ligands and the rhodium complex falls apart.

The oxidizing agent used is pure oxygen or oxygen-containing gas mixtures, in particular air. However, it is also possible to use other oxidizing agents, such as hydrogen peroxide, hydrogen peroxide-forming compounds, hypochlorite, chromates or permanganates.

The oxidation may be carried out either under atmospheric pressure, or else under elevated pressure. Useful pressures are from 0.1 to 2.0, in particular from 0.2 to 1 and in particular from 0.3 to 0.7 MPa.

The oxidation time is generally from 0.5 to 24 hours. The exact oxidation time depends on the content of the complexing ligand in the organic phase and may be determined by simple preliminary experiments. The course of the oxidation reaction is determined by gas chromatography determination of the complexing ligand content. As soon as the complexing ligand has completely reacted to give the corresponding oxide, the oxidation reaction is ended.

In a proven embodiment, a suitable reactor, for example, a stirred reactor equipped with an inlet nozzle and frit attachment or a tubular reactor provided with a gas distributor plate, which may contain a random packing, is charged with the organic phase and the oxygen or oxygen-containing gas mixture is passed upward through the organic phase.

The organic phase obtained after the oxidative treatment is then extracted with an aqueous solution of a water-soluble complexing ligand. The water-soluble complexing ligands are generally phosphines of the formula

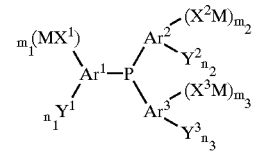

$Ar^1$, $Ar^2$ and $Ar^3$ are each a phenyl or naphthyl group, $Y^1$, $Y^2$ and $Y^3$ are each a straight-chain or branched alkyl group having from 1 to 4 carbon atoms, an alkoxy group, a halogen atom, an OH, CN, $NO_2$ or $R^7R^8N$ group, where $R^7$ and $R^8$ are each a straight-chain or branched alkyl group having from 1 to 4 carbon atoms, $X^1$, $X^2$ and $X^3$ are each a carboxylate ($COO^-$) and/or sulfonate ($SO_3^-$) radical, $n_1$, $n_2$ and $n_3$ are identical or different numbers from 0 to 5, M is an alkali metal ion, the equivalent quantity of an alkaline earth metal or zinc ion or an ammonium or quaternary alkylammonium ion of the formula $N(R^9R^{10}R^{11}R^{12})^+$, where $R^9$, $R^{10}$, $R^{11}$ and $R^{12}$ are each a straight-chain or branched alkyl group having from 1 to 4 carbon atoms, and $m_1$, $m_2$ and $m_3$ are identical or different integers from 0 to 3, and at least one number $m_1$, $m_2$ or $m_3$ is equal to or greater than 1.

The aqueous solution contains from 1 to 40, in particular from 10 to 20, preferably from 10 to 15% by weight of water-soluble complexing ligands, based on the aqueous solution.

The aqueous solution comprising the complexing ligands is used in such a quantity that the molar ratio of rhodium to phosporus III is from 1:1 to 1:200, preferably 1:10 to 1:20. The concentration of water-soluble ligands in the aqueous solution is chosen taking into account the desired molar ratio of rhodium to phosphorus III and against the background that the organic and aqueous phases should be present in a quantity ratio suitable for phase separation. In general, the volume ratio of organic to aqueous phase is from 30:70 to 70:30.

The extraction of the rhodium from the organic into the aqueous phase is carried out at elevated pressure and elevated temperature. In general, pressures of from 1 to 20 MPa, preferably from 1 to 10 MPa, in particular from 2.5 to 5 MPa and at temperatures of from 20 to 200° C., preferably from 50 to 150° C., in particular from 120 to 140° C. are employed.

The extraction is carried out either under the autogenous pressure, under pressurization of an inert gas, for example, nitrogen or a noble gas, or under synthesis gas pressure. The extraction time is generally from 0.5 to 5 hours.

It is particularly advantageous to carry out the extraction in the presence of synthesis gas. The composition of the synthesis gas, i.e. the ratio of hydrogen to carbon monoxide, may vary within a wide range. In general, the molar ratio of hydrogen to carbon monoxide is from 1:10 to 10:1. Mixtures which comprise hydrogen and carbon monoxide in a molar ratio of 1:1 are particularly suitable.

The extraction with aqueous complexing ligand solution under synthesis gas conditions leads to water-soluble rhodium complexes which, as well as the complexing ligands, also contain carbon monoxide and hydrogen in complexed form. Catalytic activity is ascribed to such rhodium complexes and the aqueous catalyst solution obtained after phase separation may be used without further treatment for hydroformylating olefins by the biphasic process, as disclosed, for example, by DE-C-26 27 354.

However, it is also possible to subject the aqueous rhodium-containing solution obtained by the process according to the invention to a further oxidation after adding a water-soluble salt of a carboxylic acid having from 7 to 22 carbon atoms in excess, based on rhodium, a process disclosed, for example, by EP-B1-0 255 673 and EP-B1-0 367 957. Rhodium can be precipitated from this aqueous solution as a sparingly water-soluble or insoluble compound, for example, in the form of rhodium 2-ethylhexanonate, and be used in a hydroformylation process carried out monophasically in the organic phase. Such a hydroformylation process is disclosed, for example, by EP-B1-0 188 246.

As disclosed by EP-B1-0 255 673, useful oxidizing agents are preferably oxygen or oxygen-containing gas mixtures, for example air. However, it is also possible to use other oxidizing agents, such as hydrogen peroxide, hydrogen peroxide-forming compounds, hypochlorite, chromates or permanganates. The oxidative treatment leads to decomposition of the rhodium complex containing the water-soluble ligands by the formation of phosphorus (V) oxide compounds which are no longer capable of forming complexes from the water-soluble phosphines used in the extraction step. During the oxidation procedure, rhodium precipitates in the form of water-insoluble compounds, presumably as rhodium carboxylate. The oxidation is carried out at a temperature of from 50 to 200° C. at atmospheric pressure or at elevated pressure of from 0.1 to 2.0 MPa over a period of from 0.5 to 24 hours. In an extension of the teaching of EP-B1-0 255 673 and EP-B1-0 367 957, the aqueous solution is extracted after the oxidation step using an organic solvent comprising an organic phosphine or diphosphine. The organic solvent used is an aliphatic hydrocarbon having from 6 to 12 carbon atoms, an aromatic hydrocarbon having from 6 to 12 carbon atoms, preferably benzene, toluene or the isomeric xylenes, ethers, for example, diethyl ether, dibutyl ether, or alcohols, for example, butanol, the isomeric pentanols, ethylene glycol or diethylene glycol. The phosphines or diphosphines used may be, for example, triphenylphosphine, tributylphosphine, tripropylphosphine, triethylphosphine, trioctylphosphine, diethylphenylphosphine, diphenylethylphosphine, diphenyl-(dimethylamino)phenyl-phosphine, methylcyclohexylanisylphosphine, 2,2'-bis ((diphenylphosphino)methyl)-1,1'-biphenyl, 1,2-bis (diphenylphosphino)ethane or 2,2'-bis((diphenylphosphino) methyl)-1,1'-binaphthyl.

The extraction of this solution using phosphines or diphosphines dissolved in an organic solvent allows rhodium to be transferred virtually quantitatively from the aqueous into the organic phase.

The extraction of the rhodium from the aqueous into the organic phase is carried out under elevated pressure and elevated temperature. In general, pressures of from 1 MPa to 20 MPa, preferably from 1 MPa to 10 MPa, in particular from 2.5 MPa to 5 MPa and temperatures of from 20° C. to 200° C., preferably from 50° C. to 150° C., in particular from 120° C. to 140° C. are employed.

The extraction is carried out either under autogenous pressure, under pressurization of an inert gas, for example, nitrogen or a noble gas, or under synthesis gas pressure. The extraction time is generally from 0.5 to 5 hours.

It is particularly advantageous to carry out the extraction in the presence of synthesis gas. The composition of the synthesis gas, i.e. the ratio of hydrogen to carbon monoxide, may vary within a wide range. In general, the molar ratio of hydrogen to carbon monoxide is from 1:10 to 10:1. Mixtures which comprise hydrogen and carbon monoxide in a molar ratio of 1:1 are particularly suitable.

The organic solution comprising the complexing ligands is used in such a quantity that the molar ratio of rhodium to phosporus III is from 1:1 to 1:200, preferably 1:10 to 1:20. The concentration of ligands in the organic solution is chosen taking into account the desired molar ratio of rhodium to phosphorus III and against the background that the organic and aqueous phases should be present in a quantity ratio suitable for phase separation. In general, the volume ratio of organic to aqueous phase is from 30:70 to 70:30.

The rhodium-containing organic solution obtained by this method can be used as the catalyst solution in the hydroformylation process carried out homogeneously, as disclosed, for example, by EP-B1-0 188 246.

The process according to the invention can be used with great success to remove and recover rhodium from the products of hydroformylation of terminal and internal olefins having more than 3 carbon atoms. When branched olefin starting materials are used, the process according to the invention is particularly suitable for removing rhodium from the reaction products which [lacuna] from the hydroformylation of i-heptene, diisobutylene, tri- and tetrapropylene or of C8-olefins commercially available under the description Dimersol. When unbranched olefins are used in the hydroformylation reaction, the work up process according to the invention can be used with particular success with hydroformylation products of propylene, n-butene, n-pentene and n-hexene, although the absolute rhodium concentrations are generally lower.

The process according to the invention can be used with great success when hydroformylation steps hitherto carried out under cobalt catalysis are converted to the rhodium method, a process disclosed by EP-0 805 138, which is a further development of the process according to EP-0 111 257.

The process according to the invention may enable more than 95% of the rhodium originally present to be recovered. The cobalt content in the concentrated rhodium solution obtained is less than 1%, based on the sum of the metals rhodium and cobalt.

It will be appreciated that the process according to the invention is not restricted to the work up of solutions which, as well as rhodium, also contain cobalt compounds as impurities. It can also be used with catalyst solutions which stem from a process carried out under exclusive rhodium catalysis.

The nonlimiting examples which follow illustrate the invention.

1$^{st}$ EXAMPLE

Work Up of a Used Rhodium/Triphenylphosphine-Containing Solution 1 000 g of a used catalyst solution having the following composition: 55% by weight of n-butyraldehyde, 2% by weight of triphenylphosphine oxide, 6.3% by weight of triphenylphosphine, 36.2% by weight of high-boilers (generally aldol condensation products of butyraldehyde) and 0.5% by weight of low-boilers (generally hydrocarbons having from 3 to 7 carbon atoms) and comprising 699 mg of rhodium (6.79 mmol) and 234 mg of cobalt (3.97 mmol) are diluted by mixing with 1 000 g of fresh n-butyraldehyde in a 4 l three-necked flask and then extracted twice with 100 g of 65% phosphoric acid for 30 minutes at 22° C. each time. The phases are separated under gentle stirring likewise within 30 minutes. The organic phase is then washed twice with 50 g of deionized water each time which had been set using 3 ml of NaOH (10% strength) to a pH of 5.8. After subsequent phase separation, the remaining organic phase is transferred to a 4 l three-necked flask equipped with a frit attachment and frit filter and aerated with 150 l/h of air at 55° C. over 12 hours at 55° C. After the oxidation had ended, 1969 g of organic phase were obtained. The organic phase is transferred together with 199.8 g of an aqueous solution of trisodium tri(m-sulfophenyl)phospine (TPPTS) (corresponds to 101.9 mmol of P III, Rh: P=1:15) into a 5 l steel autoclave and stirred in intensively for 3 hours at 5 MPa of $CO/H_2$ pressure at 125° C. The reaction mixture is then transferred to a 4 l three-necked flask equipped with a lower outlet and lower aqueous phase (144.2 g) is removed from the upper organic phase (1979 g). The aqueous TPPTS solution contains 687.7 mg of rhodium, corresponding to 98.4% of the rhodium quantity originally present in the starting solution. The cobalt content in the aqueous TPPTS solution was below the analytical detection limit.

2$^{nd}$ EXAMPLE

Hydroformylation of Propylene Using the Rh/ TPPTS Solution Obtained in Example 1

The Rh/TPPTS solution (P:Rh=14:1) obtained according to example 1 is adjusted by adding fresh TPPTS to a P:Rh ratio of 100:1. The rhodium content is 260 ppm. The solution is charged into a 0.2 l stainless steel autoclave. The 0.2 l stainless steel autoclave equipped with a stirrer is charged with propylene and a $CO/H_2$ mixture consisting of equal volume fractions in such a quantity as 10 l/h (STP) of off gas may be withdrawn from the reactor [l/h (STP) means 1 liter of off gas under atmospheric conditions (20° C. and 1 at) per hour]. At the same time, 300 ml per hour of aqueous catalyst solution are circulated through the reactor. The hydroformylation is carried out semicontinuously over 8 hours. The remaining reaction parameters and the results of the hydroformylation are given in table 1.

TABLE 1

Hydroformylation of propylene in the presence of a worked-up catalyst solution

| | |
|---|---|
| Experiment duration [h] | 8 |
| Temperature [° C.] | 122 |
| Pressure [bar] | 50 |
| Rh content [mg/kg] | 260 |
| P (III) content [mmol/kg] | 263 |
| Ligand/Rh | 100 |
| C3 introduction rate [g/h] | 40 |
| Activity [mol of aldehyde/mol of Rh · min] | 15.08 |
| Productivity [kg of aldehyde/l cat. sol. · h] | 0.213 |
| Conversion [%] | 37 |
| n/i ratio | 93/7 |

3$^{rd}$ EXAMPLE

Comparative Hydroformylation Example

A freshly prepared TPPTS solution is installed with 260 ppm of rhodium acetate in the 0.2 l stainless steel autoclave. The P:Rh ratio is 100:1. Otherwise, the hydroformylation reaction is carried out as in example 2. The remaining reaction parameters and the results of the hydroformylation are given in table 2.

TABLE 2

Hydroformylation of propylene in the presence of a fresh catalyst solution

| | |
|---|---|
| Experiment duration [h] | 8 |
| Temperature [° C.] | 122 |
| Pressure [bar] | 50 |
| Rh content [mg/kg] | 260 |
| P (III) content [mmol/kg] | 265 |
| Ligand/Rh | 100 |
| C3 introduction rate [g/h] | 40 |
| Activity [mol of aldehyde/mol of Rh · min] | 15.53 |
| Productivity [kg of aldehyde/l cat. sol. · h] | 0.216 |
| Conversion [%] | 38 |
| n/i ratio | 93/7 |

As comparison of tables 1 and 2 shows, the work up process according to the invention delivers a catalyst solution (table 1) which has virtually the same activity, productivity and conversion numbers as a freshly prepared catalyst solution using a fresh rhodium quantity (table 2).

What is claimed is:

1. A process for recovering rhodium from organic solutions which comprise rhodium complexes and cobalt complexes with or without complexing ligands, comprising extracting the organic solution with an aqueous solution of a phosphate of the formula $(O)P(OR^1)(OR^2)(OR^3)$, wherein $R^1$, $R^2$ and $R^3$ are individually selected from the group consisting of hydrogen, alkyl of 1–10 carbon atoms and a substituted or unsubstituted aryl of 6–10 carbon atoms, with the aryl substituted by alkyl of 1–4 carbon atoms, or with a phosphonate of the formula $R^4P(O)(OR^5)(OR^6)$, where $R^4$, $R^5$ and $R^6$ are individually hydrogen, alkyl of 1–10 carbon atoms and aryl of 6–10 carbon atoms unsubstituted or substituted by alkyl of 1–4 carbon atoms, and the rhodium complexes remain in the organic phase;

washing the organic phase with water at a pH of 0 to 8;

treating the organic phase after phase separation with an oxidizing agent at a temperature of 0 to 100° C.;

treating the organic phase with an aqueous solution of a water-soluble arylphosphine at elevated temperature and elevated pressure;

and removing the rhodium-containing aqueous solution from the organic phase by phase separation.

2. The process of claim 1, wherein the organic phase is extracted with the aqueous solution of the phosphate or phosphonate as defined in claim 1 at atmospheric pressure and at a temperature of from 0 to 100° C.

3. The process of claim 1, wherein the organic phase is extracted with the aqueous solution of the phosphate or phosphonate as defined in claim 1 at a pressure of from 0.5 to 20 MPa and at a temperature of from 100 to 200° C.

4. The process of claim 1, wherein $R^1$, $R^2$, $R^3$, $R^4$, $R^5$ and $R^6$ are individually alkyl of 1 to 5 carbon atoms.

5. The process of claim 1, wherein a phosphoric acid, trimethyl phosphate or methyl dimethylphosphonate extractant is used.

6. The process of claim 1, wherein the water wash is effected at a pH of from 4 to 8.

7. The process of claim 1, wherein the organic phase is oxidized with a member selected from the group consisting of oxygen, oxygen-containing gas mixtures, hydrogen peroxide, hydrogen peroxide-forming compounds, hypochlorite, chromates and permanganates.

8. The process of claim 1, wherein the oxidizing agent used is air.

9. The process of claim 1, wherein the oxidation is carried out at a temperature of from 30 to 60° C.

10. The process of claim 1, wherein the oxidation is carried out at a pressure of from 0.1 to 2.0 MPa.

11. The process of claim 1, wherein the organic phase obtained after oxidative treatment is extracted with an aqueous solution of a phosphine of the formula:

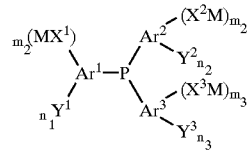

wherein $Ar^1$, $Ar^2$ and $Ar^3$ are individually phenyl or naphthyl, $Y^1$, $Y^2$ and $Y^3$ are individually selected from the group consisting of alkyl of 1 to 4 carbon atoms, alkoxy, halogen, OH, —CN, —NO$_2$ and $R^7R^8N$—, where $R^7$ and $R^8$ are individually alkyl of 1 to 4 carbon atoms, $X^1$, $X^2$ and $X^3$ are individually carboxylate (COO$^-$) or sulfonate (SO$_3^-$), $n_1$, $n_2$ and $n_3$ are individually integers from 0 to 5, M is selected from the group consisting of an alkali metal ion, the equivalent quantity of an alkaline earth metal, zinc ion, an ammonium and quaternary alkylammonium ion of the formula $N(R^9R^{10}R^{11}R^{12})^+$, where $R^9$, $R^{10}$, $R^{11}$ and $R^{12}$ are individually alkyl of 1 to 4 carbon atoms, and $m_1$, $m_2$ and $m_3$ are individually integers from 0 to 3, and at least one of $m_1$, $m_2$ or $m_3$ is equal to or greater than 1.

12. The process of claim 11, wherein the extraction is carried out at pressures of from 1 to 20 MPa, and at temperatures of from 20 to 200° C.

13. The process of claim 10, wherein the extraction is carried out in the presence of synthesis gas.

* * * * *